(12) United States Patent
Qian et al.

(10) Patent No.: US 8,809,319 B2
(45) Date of Patent: Aug. 19, 2014

(54) SUBSTITUTED 8OXA-10,11-DIHYDROIMIDAZO[2,3-A]BICYCLO[3.2.1]OCT- 3-ENES AND USE THEREOF AS AN INSECTICIDE

(75) Inventors: Xuhong Qian, Shanghai (CN); Zhong Li, Shanghai (CN); Xusheng Shao, Shanghai (CN); Xiaoyong Xu, Shanghai (CN); Zhiping Xu, Shanghai (CN); Gonghua Song, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 13/514,460

(22) PCT Filed: Dec. 9, 2010

(86) PCT No.: PCT/CN2010/079591
§ 371 (c)(1),
(2), (4) Date: Jun. 7, 2012

(87) PCT Pub. No.: WO2011/069456
PCT Pub. Date: Jun. 16, 2011

(65) Prior Publication Data
US 2012/0245126 A1    Sep. 27, 2012

(30) Foreign Application Priority Data
Dec. 9, 2009   (CN) .......................... 2009 1 0258534

(51) Int. Cl.
*A61K 31/553* (2006.01)
*C07D 223/14* (2006.01)

(52) U.S. Cl.
USPC .................. 514/211.11; 540/593; 546/281.7; 548/202; 549/429

(58) Field of Classification Search
CPC ........................... A61K 31/553; C07D 223/14
USPC .................. 514/211.11; 540/593; 546/281.7; 548/202; 549/429
See application file for complete search history.

(56) References Cited

U.S. PATENT DOCUMENTS

| | | | |
|---|---|---|---|
| 4,742,060 A | 5/1988 | Shiokawa et al. |
| 4,831,036 A | 5/1989 | Wolf et al. |
| 4,849,432 A | 7/1989 | Shiokawa et al. |
| 4,876,263 A | 10/1989 | Shiokawa et al. |
| 4,914,113 A | 4/1990 | Shiokawa et al. |

FOREIGN PATENT DOCUMENTS

| | | |
|---|---|---|
| CN | 101747320 | 6/2010 |
| EP | 0192060 | 8/1986 |
| EP | 0235725 | 9/1987 |
| EP | 0247477 | 12/1987 |
| EP | 0296453 | 12/1988 |
| EP | 0315826 | 5/1989 |
| EP | 0386565 | 9/1990 |
| EP | 0580553 | 1/1994 |
| EP | 0685477 | 12/1995 |
| EP | 1031556 | 8/2000 |
| JP | 62292765 | 12/1987 |
| JP | 7242633 | 9/1995 |
| JP | 8259568 | 10/1996 |
| JP | 8291171 | 11/1996 |
| WO | WO 2010/069266 | * 6/2010 |

OTHER PUBLICATIONS

Shao et al., "Divalent and Oxabridged Neonicotinoids Constructed by Dialdehydes and Nitromethylene Analogues of Imidacloprid: Design, Synthesis, Crystal Structure, and Insecticidal Activities,"0 Journal of Agricultural and Food Chemistry, vol. 58, No. 5 (2010), published on Web Dec. 11, 2009, p. 2696-2702.

International Search Report for international application No. PCT/CN2010/079591, dated Mar. 10, 2011 (4 pages).

* cited by examiner

*Primary Examiner* — Douglas M Willis
(74) *Attorney, Agent, or Firm* — Hamre, Schumann, Mueller & Larson, P.C.

(57) ABSTRACT

Nitromethylene analogues of imidacloprid and divalent and oxabridged heterocyclic neonicotinoid compounds constructed by dialdehydes, preparation methods and uses thereof are disclosed. Compounds represented by formula (A) or (B), their optical isomers or agrochemically acceptable salts are provided. Agrochemical compositions comprising the said compounds, their optical isomers or agrochemically acceptable salts, the uses of the said agrochemical compositions and the preparation methods of the said compounds, their optical isomers or agrochemically acceptable salts are also disclosed. The compounds and their derivatives have high insecticidal activities to several farming and forestry pests including homoptera and lepidoptera pests, such as aphis, fulgorid, whitefly, leafhopper, common thrips, cotton bollworm, cabbage caterpillar, cabbage moth, cotton leafworm and armyworm.

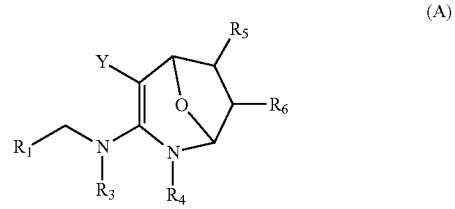

(A)

15 Claims, No Drawings

SUBSTITUTED 8-OXA-10,11-DIHYDROIMIDAZO[2,3-A]BICYCLO[3.2.1]OCT-3-ENES AND USE THEREOF AS AN INSECTICIDE

CROSS-REFERENCE TO RELATED APPLICATIONS (Not applicable)

STATEMENT REGARDING FEDERALLY SPONSORED RESEARCH OR DEVLOPMENT (Not applicable)

THE NAMES OF THE PARTIES TO A JOINT RESEARCH AGREEMENT INCORPORATION-BY (Not applicable)

BACKGROUND

1. Field

The present invention relates to a novel nicotine related insecticide, and the preparation methods and applications thereof. In particular, the present invention relates to nitromethylene analogues of imidacloprid and divalent and oxabridged heterocyclic nicotine related compounds (or neonicotinoid compounds) constructed by dialdehydes, and the preparation methods thereof.

2. Description of Related Art

Novel nicotine related pesticides, as represented by Imidacloprid, have high insecticidal activity, a broad insecticidal spectrum, and low toxicity for mammals and aquatic animals, favorable systematic properties and suitable in-field stability as well as environmental friendliness; therefore, have become an important hot spot area for new agrochemical discovery. Subsequently, a series of nicotine related insecticides, such as thiacloprid, clothianidin, thiamethoxam, acetamiprid, nitenpyram, and dinotefuran have been discovered in succession (see European Patents 247477, 296453, 685477, 235725, 235725, 315826, 192060, 244777, 0386565, 580553, and 1031556, and Japanese Patents 62292765, 8259568, 8291171, and 7242633).

However, because the frequent and excessive use of imidacloprid has caused serious problems of resistance and the structural similarity of nicotine related has brought on cross-resistance thereamong, the application of this class of compounds has been restricted to a certain extent and the development of new compounds of this class is constrained. Meanwhile, nicotine related compounds are primarily insecticidal against homopterans and coleopterans, and its relatively narrow insecticidal spectrum has also restricted the application thereof in the pest control.

Therefore, it is urgent in the art to structurally modify nitromethylene compounds with high activity for producing a new, even more effective insecticide, resolving the resistance problems of nicotine related insecticides, enlarging the insecticidal spectrum, and applying the same to insecticidal compositions.

BRIEF SUMMARY

The present invention provides a new, more effective insecticide, thereby resolving the resistance problems of nicotine related insecticides, enlarging the insecticidal spectrum, and resolving the problems existed in the art.

One objective of the present invention is to provide a compound that is highly effective in pest control, and the preparation method thereof.

Another objective of the present invention is to provide protection for preventing crops during the period of growth and harvest from being attacked and invaded by insects.

BRIEF DESCRIPTION OF THE SEVERAL VIEWS OF THE DRAWING(S)

(Not applicable)

DETAIL DESCRIPTION

In one aspect, the present invention provides an oxabridged heterocyclic nicotine related compound, which is selected from the compounds of Formula (A) or (B), or an optical isomer or agrochemically acceptable salt thereof:

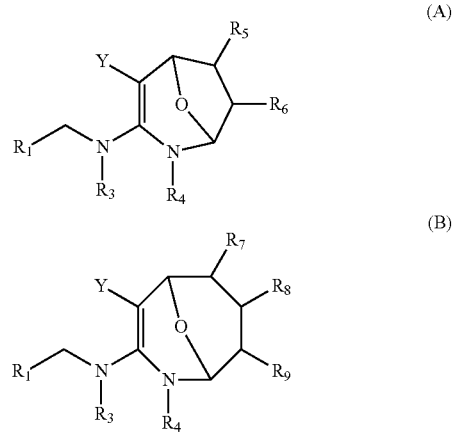

Wherein:

$R_1$ is a nitrogen-, oxygen-, and/or sulfur-containing five- or six-membered heterocycle; a halogenated nitrogen-, oxygen-, and/or sulfur-containing five- or six-membered heterocycle; or a substituted or unsubstituted phenyl, wherein the substituent is selected from one or more of the following group: a halogen, a $C_{1-4}$ halogenated alkyl, or a $C_{1-4}$ chlorinated alkoxy;

$R_3$ and $R_4$ are each independently: hydrogen; $C_{1-6}$ alkyl; allyl; benzyl; $C_{1-4}$ alkoxy-$C_{1-4}$ alkyl; $C_{1-4}$ alkoxy-carbonyl; phenoxycarbonyl; $C_{2-6}$ alkynyl-carbonyl; $C_{2-3}$ alkenyl-carbonyl;

$C_{3-6}$ cycloalkyl-carbonyl; benzoyl; or a benzoyl, furanyl-carbonyl, or N,N-dimethylcarbonyl substituted by one or more substituents selected from halogen atoms, $C_{1-4}$ alkyl, $C_{1-4}$ halo-alkyl, $C_{1-4}$ alkoxy, and $C_{1-4}$ alkyl-carbonyl; or $R_3$ and $R_4$ collectively form —$CH_2$—$CH_2$—, —$CH_2$—$CH_2$—$CH_2$—, or —$CH_2$—XR—$CH_2$—, wherein X is a heteroatom and R is a substituent on the heteroatom selected from: hydrogen; $C_{1-6}$ alkyl; allyl; benzyl; phenyl; $C_{1-4}$ alkoxy-$C_{1-4}$ alkyl; $C_{1-4}$ alkoxy-carbonyl; phenoxycarbonyl; $C_{2-6}$ alkynyl-carbonyl; $C_{2-3}$ alkenyl-carbonyl; $C_{3-6}$ cycloalkyl-carbonyl; benzoyl; or a benzoyl, furanylcarbonyl, or N,N-dimethylcarbonyl substituted by one or more substituents selected from halogen atoms, $C_{1-4}$ halo-alkyl, $C_{1-8}$ saturated or unsaturated alkyl or alkoxy, and $C_{1-4}$ alkyl-carbonyl;

$R_5$, $R_6$, $R_7$, $R_8$, and $R_9$ are hydrogen, saturated or unsaturated $C_{1-4}$ alkyl, halogen, $C_{1-8}$ saturated or unsaturated alkoxy, halogenated $C_{1-4}$ saturated or unsaturated alkoxy, $C_{1-4}$ alkyl-carbonyl, $C_{1-8}$ alkyl-ester, $C_{1-4}$ alkyl-sulfonate, phenyl, or benzyl; and Y is nitro, cyano, trifluoromethyl, trifluoroacetyl or trifluoromethanesulfonyl.

In a preferred embodiment, the oxabridged heterocyclic nicotine related compound is selected from the following group:

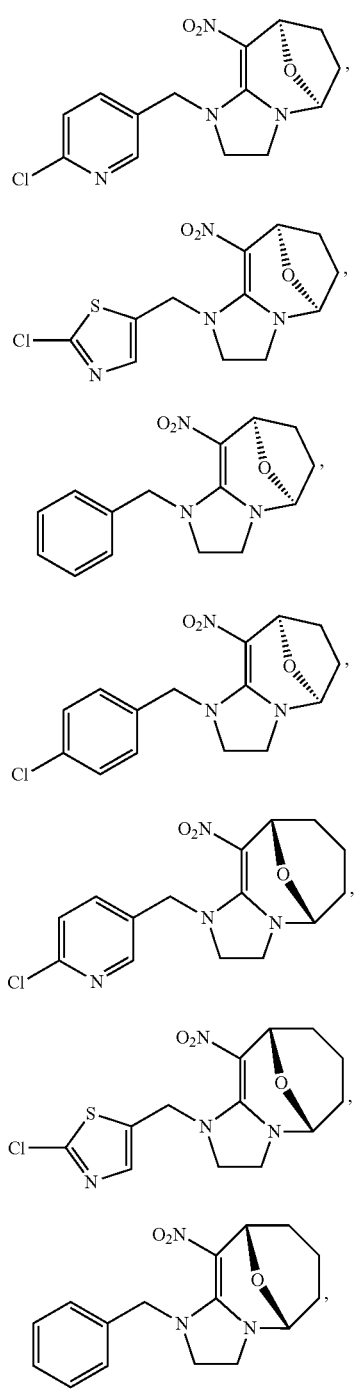

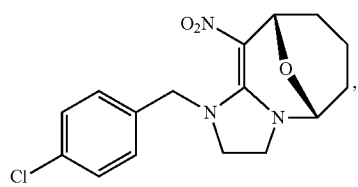

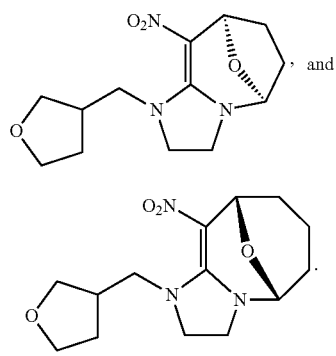

In another preferred embodiment, the oxabridged heterocyclic nicotine related compound is selected from the following group:

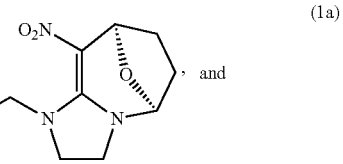

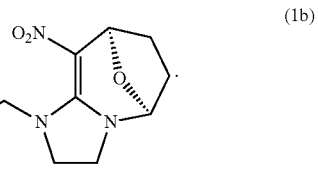

In another preferred embodiment, the oxabridged heterocyclic nicotine related compound is an antagonist of nicotinic acetylcholine receptors in insects.

In another preferred embodiment, the activity of the oxabridged heterocyclic nicotine related compounds (1a) and (1b) against imidacloprid-resistant brown plant hoppers and tobacco whiteflies is 2 to 30 times that of imidacloprid.

In another aspect, the present invention provides an agrochemical composition, which comprises:

(a) 0.001 to 99.99 wt % of the aforesaid oxabridged heterocyclic nicotine related compound, the optical isomer or agrochemically acceptable salt thereof, or the combination thereof; and (b) an agrochemically acceptable carrier and/or excipient.

In another aspect, the present invention relates to the use of said agrichemical composition in exterminating or preventing agricultural pests, sanitary pests, and pests endangering the health of animals; or as an insecticidal composition for exterminating or preventing agricultural pests, sanitary pests, and pests endangering the health of animals.

In another aspect, the present invention provides a method for exterminating and/or preventing pest, the method comprising applying said agrichemical composition to plants suffering or likely suffering from pests, and to the surrounding soil or environment thereof.

In another aspect, the present invention relates to the use of said compound, the optical isomer or agrochemically acceptable salt thereof, or the combination thereof in preparing an insecticidal composition.

In yet another aspect, the present invention provides a method for preparing said compound, or the optical isomer or agrochemically acceptable salt thereof, the method comprising the following step:

obtaining the compound of Formula (A) or (B) by reacting the compound of Formula (a) with the compound of Formula (b) or (c) at room temperature in the presence of a catalytic

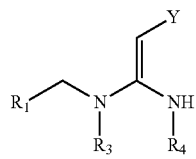
(a)

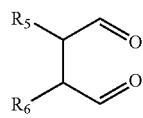
(b)

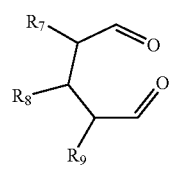
(c)

wherein, $R_1$, $R_3$, $R_4$, $R_5$, $R_6$, $R_7$, $R_8$, $R_9$, and Y are as defined above.

In a preferred embodiment, said method comprises the following steps:

obtaining the compound of Formula (1a) by conducting the following reaction for 2 to 24 hours in acetonitrile at room temperature in the presence of a catalytic amount of acid;

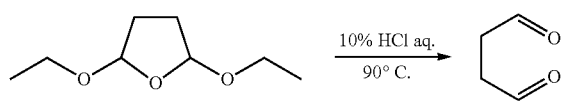

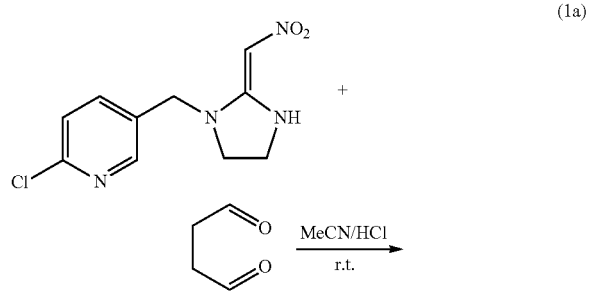
(1a)

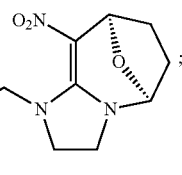

obtaining the compound of Formula (1b) by conducting the following reaction for 2 to 24 hours in acetonitrile at room temperature in the presence of a catalytic amount of acid;

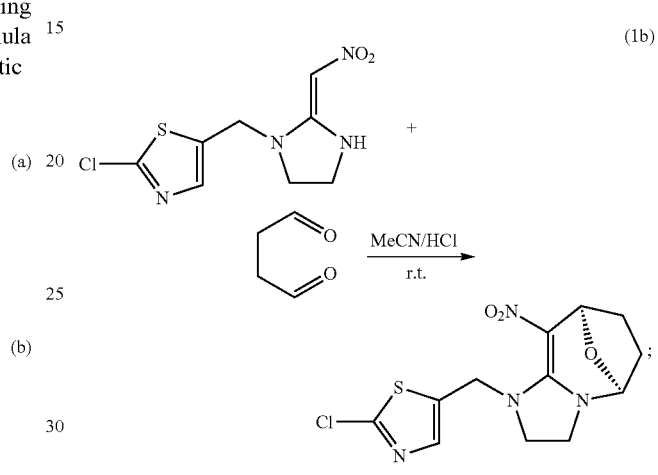
(1b)

obtaining the compound of Formula (1c) by conducting the following reaction for 2 to 24 hours in acetonitrile at room temperature in the presence of a catalytic amount of acid;

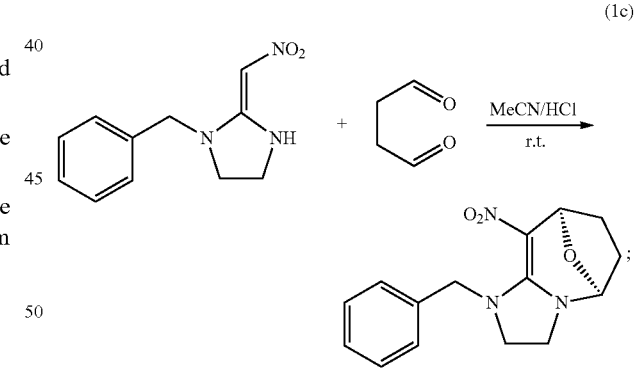
(1c)

obtaining the compound of Formula (1d) by conducting the following reaction for 2 to 24 hours in acetonitrile at room temperature in the presence of a catalytic amount of acid;

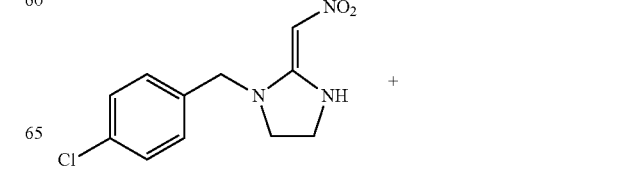
(1d)

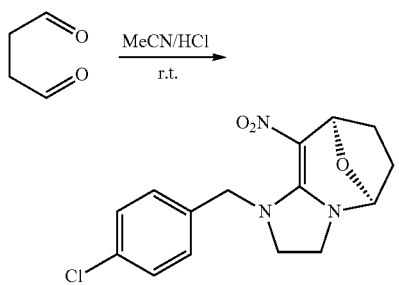

obtaining the compound of Formula (2a) by conducting the following reaction for 2 to 24 hours in acetonitrile at room temperature in the presence of a catalytic amount of acid;

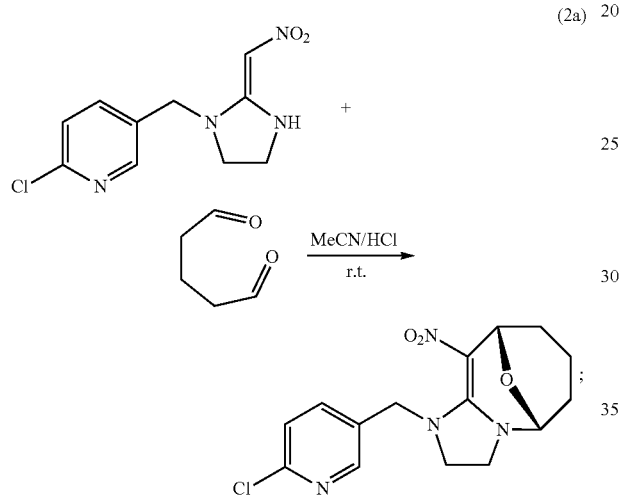

obtaining the compound of Formula (2b) by conducting the following reaction for 2 to 24 hours in acetonitrile at room temperature in the presence of a catalytic amount of acid;

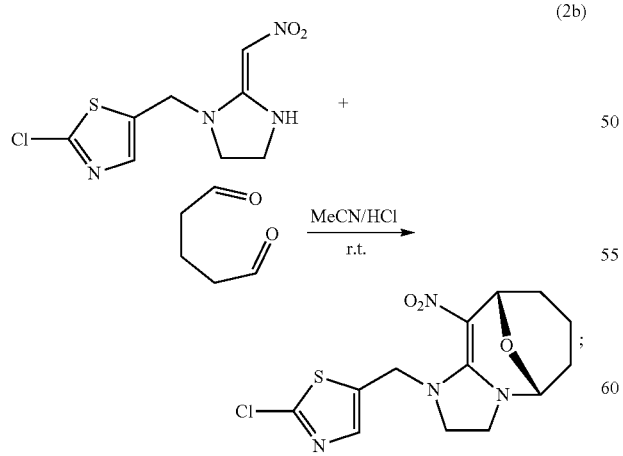

obtaining the compound of Formula (2c) by conducting the following reaction for 2 to 24 hours in acetonitrile at room temperature in the presence of a catalytic amount of acid;

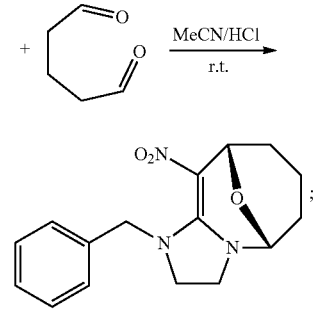

obtaining the compound of Formula (2d) by conducting the following reaction for 2 to 24 hours in acetonitrile at room temperature in the presence of a catalytic amount of acid;

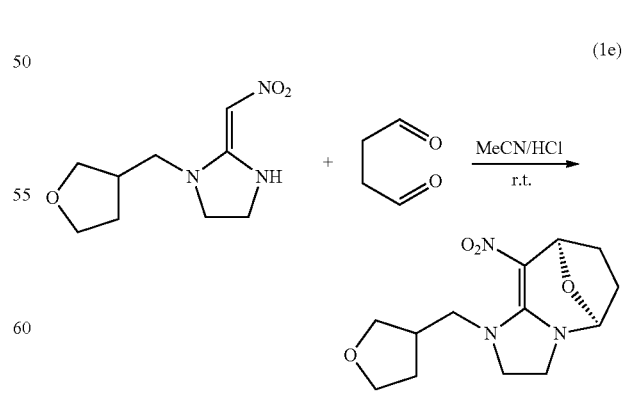

obtaining the compound of the Formula (1e) by conducting the following reaction for 2 to 24 hours in acetonitrile at room temperature in the presence of a catalytic amount of acid; and obtaining the compound of Formula (2e) by conducting the following reaction for 2 to 24 hours in acetonitrile at room temperature in the presence of a catalytic amount of acid.

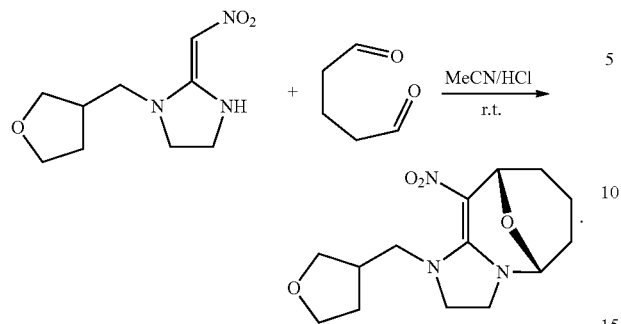

(2e)

Specific Embodiments

Through extensive and intensive research, based on the imidacloprid nitromethylene structure of existing imidacloprid nitromethylene nicotine related insecticides, the inventors of the present invention have, by reacting a dialdehyde with an imidacloprid nitromethylene compound, synthesized a novel nicotine related compound, which has a markedly improved insecticidal activity and possesses a broader insecticidal spectrum. The present inventors have accomplished the present invention based on the above.

Definitions Of Functional Groups

As used herein, the term "$C_{1-6}$ alkyl" refers to a linear or branched alkyl having one to six carbon atoms, such as methyl, ethyl, propyl, isopropyl, butyl, isobutyl, sec-butyl, tert-butyl, or analogous groups.

The term "$C_{1-4}$ alkoxy" refers to a linear or branched alkoxy having one to four carbon atoms, such as methoxy, ethoxy, propoxy, isopropoxy, butoxy, isobutoxy, sec-butoxy, tert-butoxy, or analogous groups.

The term "halogen" refers to fluorine, chlorine, bromine, or iodine. The term "halogenated" refers to a group substituted with one or more different or identical halogen atoms said above, such as trifluoromethyl, pentafluoroethyl, or analogous groups.

The term e "five- or six-membered heterocycle" refers to a five- or six-membered ring containing one or more heteroatoms selected from nitrogen, oxygen, or sulfur, such as pyridyl, thiazolyl, pyrimidyl, tetrahydrofuranyl, oxazolyl etc.

Method for Preparing the Compound of the Present Invention

The compound of the present invention can be synthesized through the reaction steps described above.

In one specific embodiment of the present invention, the method for synthesizing the compound of Formula (1a) is as follows:

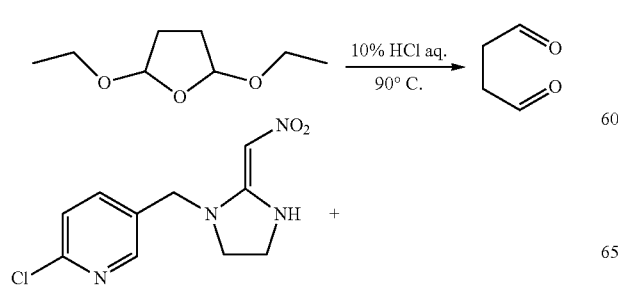

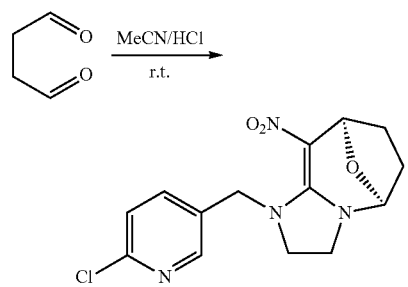

In one specific embodiment of the present invention, the method for synthesizing the compound of Formula (1b) is as follows:

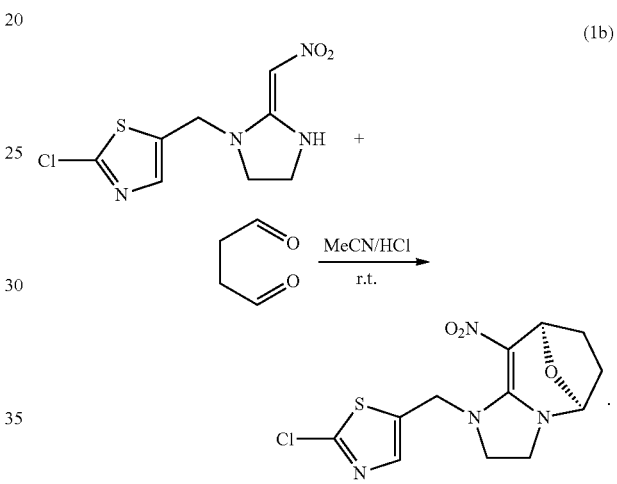

(1b)

In one specific embodiment of the present invention, the method for synthesizing the compound of Formula (1c) is as follows:

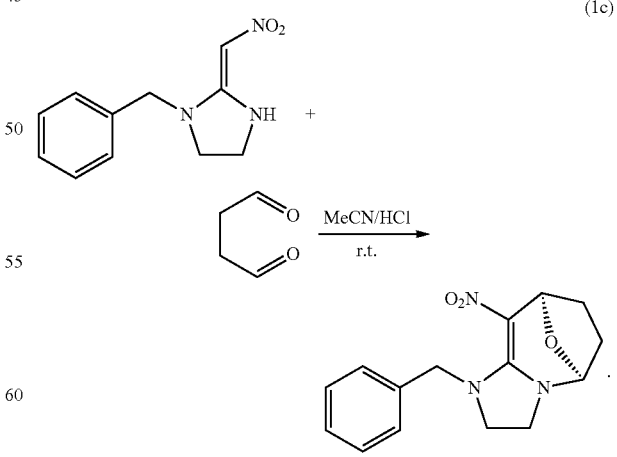

(1c)

In one specific embodiment of the present invention, the method for synthesizing the compound of Formula (1d) is as follows:

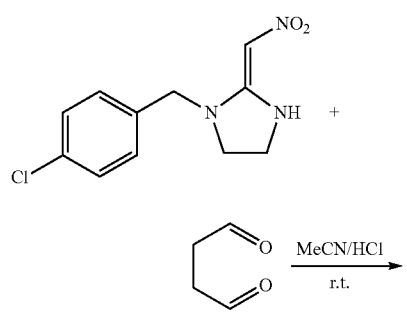

(1d)

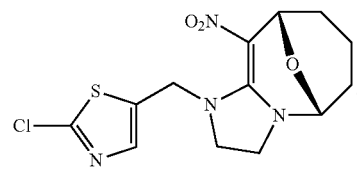

-continued

In one specific embodiment of the present invention, the method for synthesizing the compound of Formula (2c) is as follows:

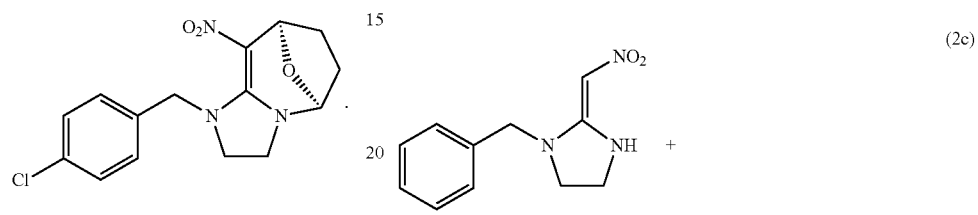

In one specific embodiment of the present invention, the method for synthesizing the compound of Formula (2a) is as follows:

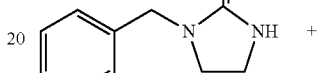

(2a)

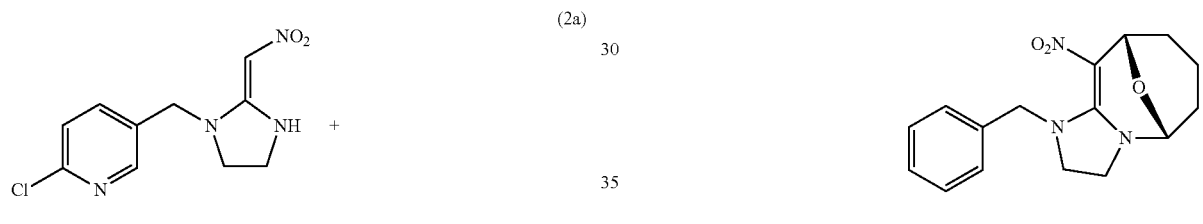

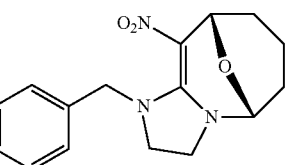

In one specific embodiment of the present invention, the method for synthesizing the compound of Formula (2d) is as follows:

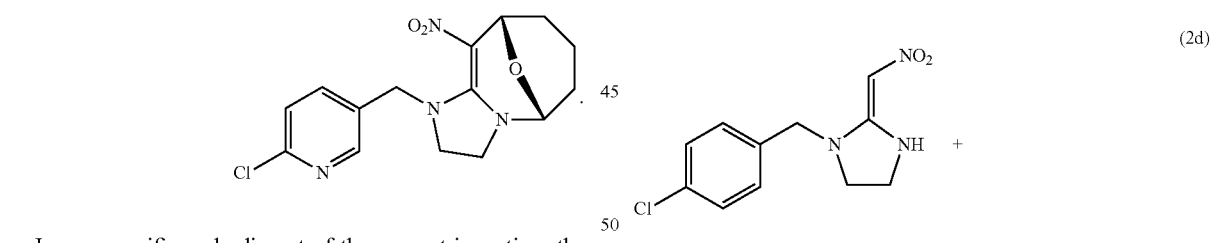

In one specific embodiment of the present invention, the method for synthesizing the compound of Formula (2b) is as follows:

(2b)

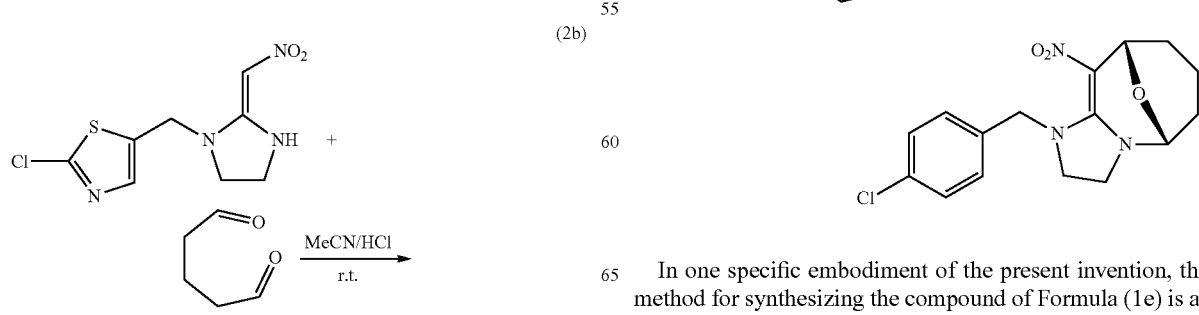

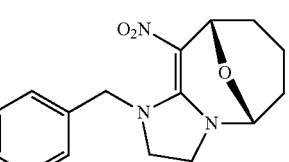

In one specific embodiment of the present invention, the method for synthesizing the compound of Formula (1e) is as follows:

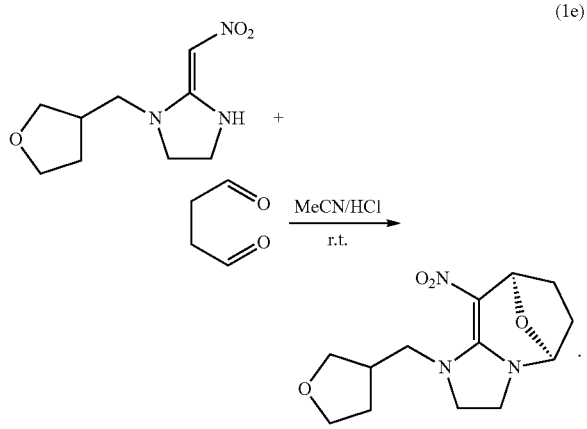

In one specific embodiment of the present invention, the method for synthesizing the compound of Formula (2e) is as follows:

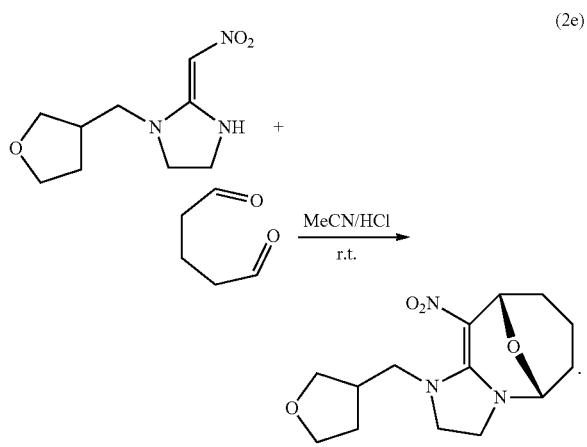

In one embodiment of the present invention, the compounds of Formulae (1a) to (1e) can be prepared by the following reactions:

A mixed solution of 2,5-diethoxy tetrahydrofuran (2 g, 12.5 mmol) and aqueous hydrochloric acid (0.1 M, 10 mL) is heated to 90° C. and reacted for one hour, and then cooled to room temperature. Acetonitrile (40 mL) and a nitromethylene analogue of imidacloprid (10 mmol) are added into the reaction, and the system is stirred at room temperature. The reaction is monitored by TLC, and after the reaction is completed, the reaction is neutralized by a saturated aqueous sodium bicarbonate. The system is extracted, the solvent is removed under reduced pressure, and column chromatography separation is performed (eluent: dichloromethane/acetone=3/1 (v/v)) to obtain a pale yellow powder, i.e., the product.

In another embodiment, the compounds of Formulae (2a) to (2e) can be prepared by the following reactions:

A nitromethylene analog of imidacloprid (5 mmol), 30 mL of acetonitrile anhydrous, 3 mL of 25% aqueous glutaraldehyde, and a catalytic amount of HCl are placed in a 50-mL round-bottomed flask. At room temperature, the reaction is stirred, and is monitored by TLC. After the reaction is completed, the system is neutralized by a saturated aqueous sodium bicarbonate, and extracted. The solvent is removed under reduced pressure, and column chromatography separation is performed (eluent: dichloromethane/acetone=3/1 (v/v)) to obtain a pale yellow powder, i.e., the product.

Insecticidal Activity of the Active Substance of the Present Invention

The term "active substance of the present invention" or "active compound of the present invention" refers to the compound of the present invention, or to the optical isomer or agrochemically acceptable salt thereof possessing markedly enhanced insecticidal activity and a broader insecticidal spectrum.

The term "agrochemically acceptable salt" means that the anion of such salt forming the agrochemically acceptable salts of insecticides is known or acceptable. Preferably, such salt is water-soluble. The suitable acid addition salts formed from the compounds of Formulas (A) and (B) include the salt formed by an inorganic acid, such as hydrochloride, phosphate, sulfate, and nitrate; and the salt formed by an organic acid, such as acetate or benzoate. The active substance of the present invention can be used to control and exterminate various of pests of agriculture and forestry plant, pests of storage cereals, pests that harm public health, pests that harm the health of animals, and the like. In the present specification, an "insecticide" represents any substance that possesses the effect of preventing or controlling all of the aforementioned pests. Examples of pests include, but are not limited to, coleoptera insects: *Sitophilus zeamais, Tribolium castaneum, Henosepilachna vigintioctomaculata, Henosepilachna sparsa, Agriotes fuscicollis, Anomala cupripes, Popillia quadriguttata, Monolepta hieroglyphica, Monochamus alternatus, Echinocnemus squameus, Basiprionota bisignata, Anoplophora chinensis, Apriona germari, Scolytus schevy*, or *Agriotes fuscicollis*; lepidoptera insects: *Lymantria dispar; Malacosoma neustria testacea, Diaphania perspectalis, Clania variegata, Cnidocampa flavescens, Dendrolimus punctatus, Orgyia gonostigma, Paranthrene tabaniformis, Spodoptera litura, Chilo suppressalis, Ostrinia nubilalis, Ephestia cautella, Adoxophyes orana, Laspeyresia splendana, Agrotis fucosa, Galleria mellonella, Plutella xylostella, Phyllocnistis citrella, Mythimna separata*; homoptera insects: *Nephotettix cincticeps, Nilaparvata lugens, Pseudococcus comstocki, Unaspis yanonensis, Myzus persicae, Aphis gossypii, Lipaphis erysimi pseduobrassicae, Stephanitis nashi*, or *Bemisia tabaci*; orthoptera insects: *Blattella germanica, Periplaneta americana, Ggllotalpa africana*, or *Locus migratoria;* or isoptera insects: *Solenopsis invicta*, or *Coptotermes formasanus*; diptera insects: *Musca domestica, Aedes aegypti, Delia platura, Culex* sp., or *Anopheles sinensis*. Pests that harm the health of animals comprise *Boophilus microplus, Haemaphysalis longicornis, Hyalomma anatolicum, Hypoderma* spp., *Fasciola hepatica, Moniezia benedeni, Ostertagia* spp., *Trypanosoma evansi, Babesia bigemina*, and the like.

The compound of the present invention is especially effective against agriculture and forestry insects having piercing-sucking or rasping-sucking mouthparts, such as aphids, leafhopper, planthoppers, thrips, whitefly, and the like.

Insecticidal Compositions Containing the Active Substance of the Present Invention A conventional method can be used to prepare an insecticidal composition from the active substances of the present invention. Such active compounds can be made into a conventional formulation, such as solutions, emulsions, suspensions, powders, foams, pastes, or granules; aerosols; natural or synthetic materials impregnated with the active substance, microcapsules in a polymer, a coating complex used for seeds; a preparation to be used together with a combustion device, such as a fumigant cartridge, fumigant jar or fumigant plate, and ULV cold mist and warm mist preparations.

These formulation can be produced using a known method, for example, mixing the active compound(s) and extenders, wherein the extenders are a diluent or carrier in the form of a liquid, a liquefied gas, or a solid, optionally with a surfactant, i.e. an emulsifying agent and/or a dispersion agent and/or a foam forming agent. For example, when water is used as an extender, an organic solvent can also be used as auxiliary solvents.

It is generally proper to use liquid solvents as a diluent or carrier, for example: aromatic hydrocarbons, such as xylene, toluene, or alkylnaphthalenes; chlorinated aromatic or chlorinated aliphatic hydrocarbons, such as chlorobenzene, vinyl chloride, or dichloromethane; aliphatic hydrocarbons, such as cyclohexane or a paraffin such as a mineral oil fraction; alcohols, such as ethanol, ethylene glycol, and the ethers and esters thereof; or ketones, such as acetone, methyl ethyl ketone, methyl isobutyl ketone, or cyclohexanone; or polar solvents used less commonly, such as dimethyl formamide, dimethyl sulfoxide, and water. A diluent or carrier in the form of a liquefied gas refers to a liquid which are gaseous at normal temperature and under atmospheric pressure, for example, aerosol propellants, such as halogenated hydrocarbons as well as butane, propane, nitrogen gas, and carbon dioxide.

Solid carriers include ground natural minerals, such as: Kaolin, clay, talc, quartz, activated clay, montmorillonite or diatomaceous earth; or ground synthetic minerals, such as highly dispersed silicic acid, alumina, and silicates. A solid carrier used for granules is crushed and graded natural zircon, such as calcite, marble, pumice, sepiolite, and dolomite, as well as granules synthesized from inorganic or organic coarse powder, and organic materials such as granules from sawdust, coconut shells, corn cobs, or tobacco stems, and the like.

Non-ionic or anionic emulsifiers can be used as emulsifying and/or foam-forming agents. Examples include: polyoxyethylene-fatty acid esters and polyoxyethylene-fatty alcohol ethers, such as alkyl aryl polyethylene glycol ethers, alkyl sulfonic acid esters, alkyl sulfuric acid esters, aryl sulfonic acid esters, and albumin hydrolysis products. Dispersion agents include, for example, lignin-sulfite waste and methyl cellulose.

In the formulations, it is possible to use an adhesive, such as carboxymethyl cellulose and a natural or synthetic polymer (e.g., gum arabic, polyvinyl alcohol, and polyvinylacetate), in the form of powders, granules, or emulsions. A coloring agent can also be used, such as an inorganic dye, (e.g., iron oxide, cobalt oxide, or Prussian blue); or an organic dye, (such as an azo dye or a metal phthalocyanine dye); and a trace nutrient, such as the salts of iron, manganese, boron, copper, cobalt, aluminum and zinc, and the like.

These active compounds of the present invention may, together with other active compounds, be made into a mixture present in a commercial formulation or a dosage form prepared from the commercial formulation; said other active compounds include, but are not limited to, insecticides, bait, bactericide, acaricides, nematocides, fungicides, growth control agents, and the like. Insecticides comprise, for example, phosphate esters, carbamic esters, pyrethrum ester, chlorinated hydrocarbons, benzoylurea, nereistoxins, and substances produced by microorganisms, such as abamectin.

In addition, these active compounds of the present invention may also, together with a synergist, be made into a mixture present in a commercial formulation or a dosage form prepared from these commercial formulations. Synergist is a compound that enhances the effects of the active compounds; the synergist is not necessary, since the active compounds are inherently active.

Generally, the formulations contain 0.001 to 99.99 wt % of the active compounds of the present invention, preferably 0.01 to 99.9 wt %, more preferably 0.05 to 90 wt %, by the weight of said insecticidal composition. The concentration of active compounds in a dosage form prepared from a commercial formulation may be varied within a broad range. The concentration of active compounds in a dosage form can be between 0.0000001 to 100% (g/v), preferably between 0.0001 and 1%.

EXAMPLES

The invention will be further illustrated below with reference to the following examples. It should be understood that these examples are merely to illustrate the present invention, but not to limit the scope of the present invention. The experimental methods with no specific conditions described in the following examples are generally performed under conventional conditions, or according to the manufacturer's instruction. Unless otherwise specified, percentages and parts are calculated by weight. Herein, "r.t." stands for room temperature.

Example 1

Synthesis of 9-((6-chloropyrid-3-yl)methyl)-4-nitro-8-oxa-10,11-dihydroimidazo-[2,3-a]-bicyclo-[3,2,1]-oct-3-ene (the compound 1a)

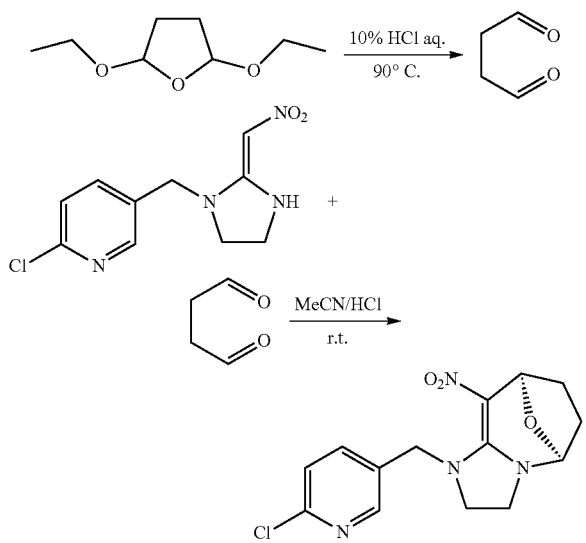

A mixed solution of 2,5-diethoxytetrahydrofuran (2 g, 12.5 mmol) and an aqueous solution of hydrochloric acid (0.1 M, 10 mL) was heated to 90° C. and reacted for one hour, and then cooled to room temperature. In the reaction, acetonitrile (40 mL) and 2-chloro-5-(2-nitromethylene-imidazolidin-1-ylmethyl)-pyridine (2.54 g, 10 mmol) were added, and the system was stirred at room temperature. The reaction was monitored by TLC, and, after the reaction was completed, the system was neutralized by in a saturated aqueous sodium bicarbonate. The system was extracted, the solvent was removed under reduced pressure, and column chromatography separation was performed (eluent: dichloromethane/acetone=3/1 (v/v)) to obtain a pale yellow powder. Yield: 53%; mp=149.0-150.0° C.; $^1$H NMR (400 Mz, DMSO-$d_6$): δ 8.35 (d, J=2.4 Hz, 1H), 7.81 (dd, $J_1$=2.4 Hz, $J_2$=8.4 Hz, 1H), 7.51 (d, J=8.4 Hz, 1H), 5.36-5.39 (s, 2H), 5.00 (d, J=15.6 Hz, 1H), 4.68 (d, J=15.6 Hz, 1H), 3.57-3.73 (m, 4H), 1.94-2.04 (m, 4H) ppm; $^{13}$C NMR (100 Mz, DMSO-$d_6$): δ 155.6, 149.7, 149.6, 139.7, 132.6, 124.5, 109.6, 87.0, 75.1, 51.2, 50.3, 46.6, 31.9, 31.7 ppm; HRMS (ES+) calculated value: $C_{14}H_{16}N_4O_3{}^{35}Cl$ (M+H)$^+$, 323.0911; measured value 323.0912. Calculated value: $C_{14}H_{16}N_4O_3{}^{37}Cl$ (M+H)$^+$, 325.0811; measured value 325.0895. Calculated value: $C_{14}H_{15}N_4O_3{}^{35}ClNa$ (M+Na)$^+$, 345.0730, calculated value 345.0722. Calculated value: $C_{14}H_{15}N_4O_3{}^{37}ClNa$ (M+Na)$^+$, 347.0701; calculated value 347.0692.

Example 2

Synthesis of 9-((2-chlorothiazol-5-yl)methyl)-4-nitro-8-oxa-10,11-dihydroimidazo-[2,3-a]-bicyclo-[3,2,1]-oct-3-ene (the compound 1b)

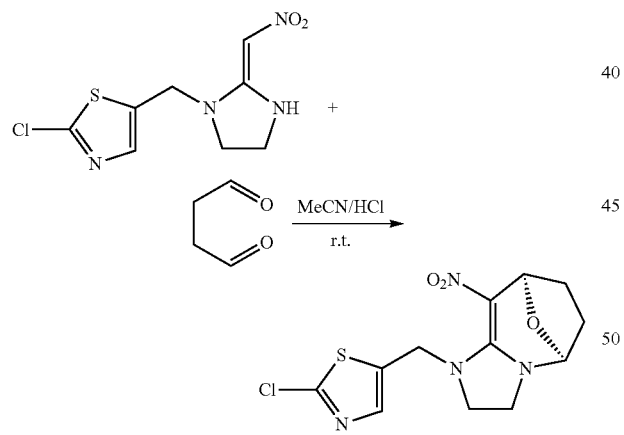

The preparation method is similar to the above method. The solvent was removed under reduced pressure, and column chromatography separation was performed (eluent: dichloromethane/acetone=3/1 (v/v)) to obtain a pale yellow solid in powder. Yield: 56%; mp=136.5-138.0° C.; $^1$H NMR (400 Mz, DMSO-$d_6$): δ 7.47 (s, 1H), 5.61 (d, J=5.2 Hz, 1H), 5.28 (d, J=15.4 Hz, 1H), 5.16 (d, J=5.00 Hz, 1H), 4.70 (d, J=15.4 Hz, 1H), 3.66-3.82 (m, 3H), 3.54-3.61 (m, 1H), 2.22-2.29 (m, 1H), 2.12-2.21 (m, 2H), 1.99-2.07 (m, 1H) ppm; $^{13}$C NMR (100 Mz, DMSO-$d_6$): δ 154.6, 154.3, 140.6, 135.1, 110.4, 87.4, 75.4, 49.6, 47.9, 46.5, 31.8, 31.8 ppm; HRMS (ES+) calculated value: $C_{12}H_{14}N_4O_3S^{35}Cl$ (M+H)$^+$, 329.0475, calculated value 329.0475. Calculated value: $C_{12}H_{14}N_4O_3S^{37}Cl$ (M+H)$^+$, 331.0446, calculated value 331.0461.

Example 3

Synthesis of 9-benzyl-4-nitro-8-oxa-10,11-dihydroimidazo-[2,3-a]-bicyclo-[3,2,1]-oct-3-ene (the compound 1c)

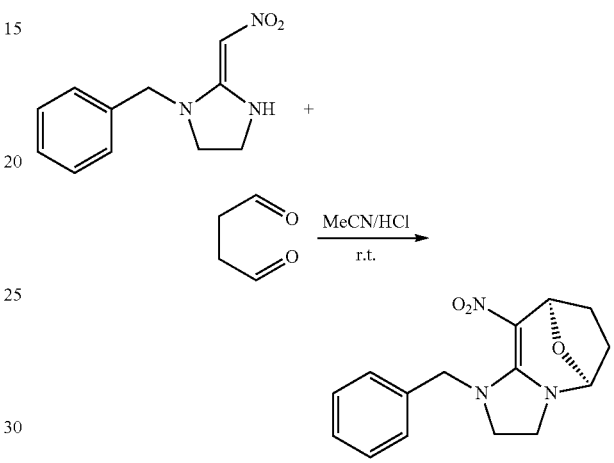

The preparation method is similar to the above method. The solvent was removed under reduced pressure, and column chromatography separation was performed (eluent: dichloromethane/acetone=3/1 (v/v)) to obtain a pale yellow solid in powder. Yield: 58%; mp=149.0-149.8° C.; $^1$H NMR (400 Mz, DMSO-$d_6$): δ 7.28-7.39 (m, 5H), 5.66 (d, J=4.3 Hz, 1H), 5.14 (d, J=4.5 Hz, 1H), 4.92-5.01 (m, 2H), 3.57-3.74 (m, 3H), 3.47-3.53 (m, 1H), 2.30-2.34 (m, 1H), 2.13-2.22 (m, 2H), 2.00-2.07 (m, 1H) ppm; $^{13}$C NMR (100 Mz, DMSO-$d_6$): δ 155.5, 135.9, 128.9, 128.2, 128.1, 87.7, 75.6, 54.4, 48.9, 47.2, 31.8, 31.6 ppm; HRMS (ES+) calculated value: $C_{15}H_{17}N_3O_3$ (M+H)$^+$, 287.1270; calculated value 287.1272.

Example 4

Synthesis of 9-(4-chloro-benzyl)-4-nitro-8-oxa-10,11-dihydroimidazo-[2,3-a]-bicyclo-[3,2,1]-oct-3-ene (the compound 1d)

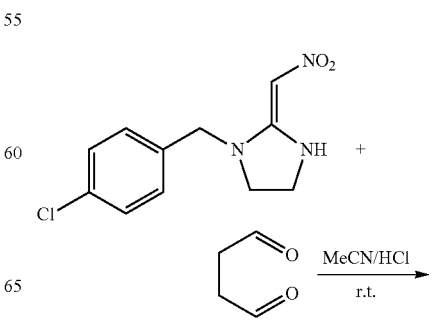

-continued

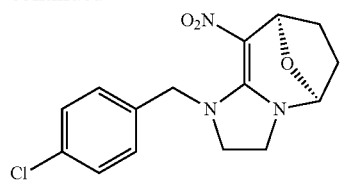

The preparation method is similar to the above method. The solvent was removed under reduced pressure, and column chromatography separation was performed (eluent: dichloromethane/acetone=3/1 (v/v)) to obtain a pale yellow solid in powder. Yield: 38%; mp=140.0-140.9° C.; $^1$H NMR (400 Mz, DMSO-d$_6$): δ 7.27-7.34 (m, 4H), 5.63 (d, J=5.4 Hz, 1H), 5.14 (d, J=5.2 Hz, 1H), 5.04 (d, J=15.1 Hz, 1H), 4.78 (d, J=15.1 Hz, 1H), 3.62-3.73 (m, 3H), 3.45-3.51 (m, 1H), 2.26-2.31 (m, 1H), 2.11-2.21 (m, 2H), 1.98-2.07 (m, 1H) ppm; $^{13}$C NMR (100 Mz, DMSO-d$_6$): δ 155.3, 134.4, 133.9, 129.6, 129.0, 110.2, 87.6, 75.5, 53.9, 49.2, 47.0, 31.8, 31.7 ppm; HRMS (ES+) calculated value: $C_{15}H_{17}N_3O_3{}^{35}Cl$ (M+H)$^+$, 322.0958; calculated value: 322.0972. Calculated value: $C_{15}H_{17}N_3O_3{}^{37}Cl$ (M+H)$^+$, 324.0929; calculated value 324.0938.

Example 5

Synthesis of 9-((tetrahydrofuran-3-yl)methyl)-4-nitro-8-oxa-10,11-dihydroimidazo-[2,3-a]-bicyclo-[3,2,1]-oct-3-ene (the compound 1e)

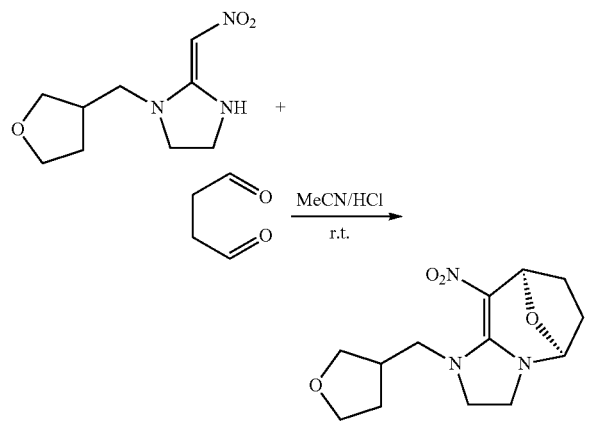

The preparation method is similar to the above method. The solvent was removed under reduced pressure, and column chromatography separation was performed (eluent: dichloromethane/acetone=3/1 (v/v)) to obtain a pale yellow solid in powder. Yield: 57%. m=126.3-127.9° C.; $^1$H NMR (400 Mz, DMSO-d$_6$) δ 5.11 (s, 1H), 5.00-5.03 (m, 1H), 4.18 (d, J=3.2 Hz, 2H), 4.05-4.25 (m, 2H), 3.85-3.96 (m, 4H), 2.25 (m, 1H), 1.66-1.81 (m, 4H), 2.35-2.40 (m, 1H), 2.17-2.21 (m, 2H), 1.93-2.01 (m, 1H) ppm; ppm; $^{13}$C NMR (100 Mz, DMSO-d$_6$): δ 81.9, 81.6, 77.9, 68.2, 53.1, 49.9, 48.0, 44.1, 36.4, 33.9, 29.5, 23.2, 19.8, ppm; HRMS (EI+) calculated value: $C_{13}H_{19}N_3O_4$ (M$^+$), 281.1376; measured value 281.1365.

Example 6

Synthesis of 10-((6-chloropyrid-3-yl)methyl)-4-nitro-9-oxa-11,12-dihydroimidazo-[2,3-a]-bicyclo-[3,3,1]-non-3-ene (the compound 2a)

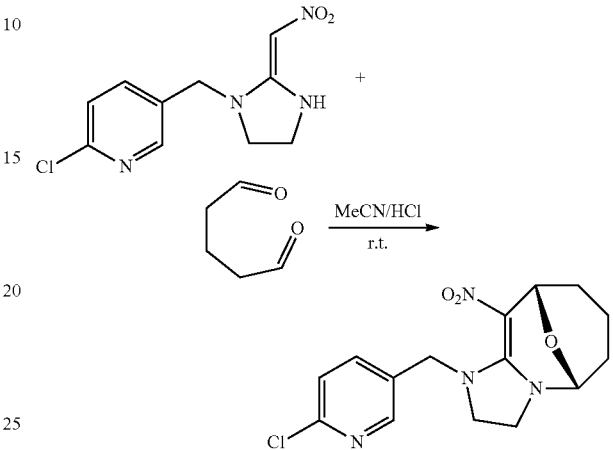

1.27 g of 2-chloro-5-(2-nitromethylene-imidazolidin-1-yl methyl)-pyridine (0.005 mol), 30 mL of acetonitrile anhydrous, 3 mL of 25% aqueous glutaraldehyde, and a catalytic amount of HCl were placed in a 50-mL round-bottomed flask. The system was stirred at room temperature. The reaction was monitored by TLC. After the reaction was completed, the system was neutralized by a saturated aqueous sodium bicarbonate, and extracted. The solvent was removed under reduced pressure, and column chromatography separation was performed (eluent: dichloromethane/acetone=3/1 (v/v)) to obtain a pale yellow powder. Yield: 76%; mp=174.7-175.4° C.; $^1$H NMR (400 Mz, DMSO-d$_6$): δ 8.38 (dd, J=0.6 Hz, J$_2$=2.4 Hz, 1H), 7.84 (dd, 2.4 Hz, J$_2$=8.4 Hz, 1H), 7.52 (dd, J$_1$=0.6 Hz, J$_2$=8.4 Hz, 1H), 5.12 (s, 1H), 5.04-5.05 (m, 1H), 4.97 (d, J=15.6 Hz, 1H), 4.71 (d, J=15.6 Hz, 1H), 3.62-3.74 (m, 4H), 1.66-1.81 (m, 4H), 1.51-1.55 (m, 1H), 1.32-1.44 (m, 1H) ppm; $^{13}$C NMR (100 Mz, DMSO-d$_6$): δ 156.6, 149.7, 149.6, 139.7, 132.9, 124.5, 105.8, 81.7, 68.9, 51.7, 50.0, 46.3, 28.8, 27.2, 14.8 ppm; HRMS (EI+) calculated value: $C_{15}H_{17}N_4O_3{}^{35}Cl$ (M+), 336.0989; calculated value 336.0988. Calculated value: $C_{15}H_{17}N_4O_3{}^{37}Cl$ (M+), 338.0960; calculated value 338.0968.

Example 7

Synthesis of 10-((2-chlorothiazol-5-yl)methyl)-4-nitro-9-oxa-11,12-dihydroimidazo-[2,3-a]-bicyclo-[3,3,1]-non-3-ene (the compound 2b)

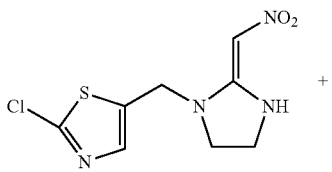

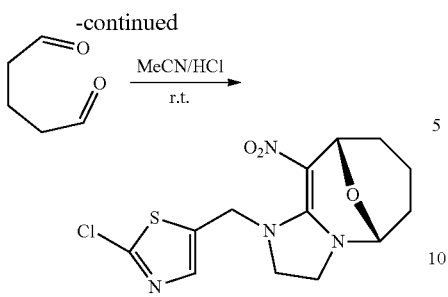

The preparation method is similar to the above method. The solvent was removed under reduced pressure, and column chromatography separation was performed (eluent: dichloromethane/acetone=3/1 (v/v)) to obtain a white solid in powder. Yield: 62%; mp=159.1-160.5° C.; $^1$H NMR (400 Mz, DMSO-$d_6$): δ 7.48 (s, 1H), 5.30 (d, J=3.2 Hz, 1H), 5.24 (d, J=15.4 Hz, 1H), 4.98 (s, 1H), 4.78 (d, J=15.4 Hz, 1H), 3.76-3.87 (m, 1H), 3.60-3.71 (m, 3H), 2.12 (d, J=14.0 Hz, 1H), 1.82-1.96 (m, 2H), 1.64-1.77 (m, 2H), 1.48-1.60 (m, 1H) ppm; $^{13}$C NMR (100 Mz, DMSO-$d_6$): δ 155.7, 154.1, 140.5, 135.6, 107.0, 82.7, 69.4, 49.4, 48.3, 46.2, 29.4, 26.5, 14.9 ppm; HRMS (EI+) calculated value: $C_{13}H_{15}N_4O_3S^{35}Cl$ (M+), 342.0553; calculated value: 342.0548. Calculated value $C_{13}H_{15}N_4O_3S^{37}Cl$ (M+), 344.0524; calculated value 344.0564.

Example 8

Synthesis of 10-benzyl-4-nitro-9-oxa-11,12-dihydroimidazo-[2,3-a]-bicyclo-[3,3,1]-non-3-ene (the compound 2c)

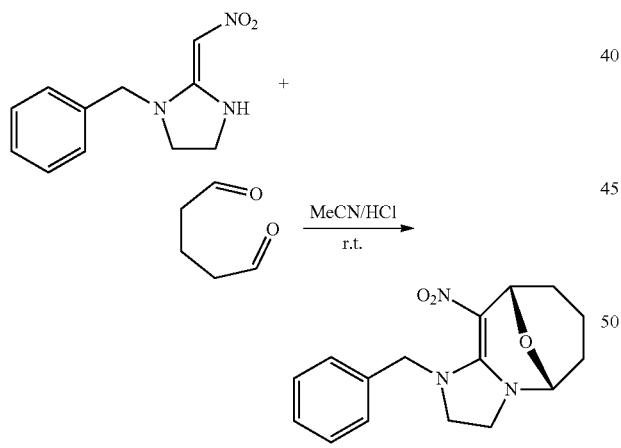

The preparation method is similar to the above method. The solvent was removed under reduced pressure, and column chromatography separation was performed (eluent: dichloromethane/acetone=3/1 (v/v)) to obtain a pale yellow solid in powder. Yield: 77%; mp=180.5-181.2° C.; $^1$H NMR (400 Mz, DMSO-$d_6$): δ 7.29-7.37 (m, 5H), 5.33 (d, J=3.1 Hz, 1H), 5.02 (d, J=15.0 Hz, 1H), 4.95 (s, 1H), 4.85 (d, J=15.0 Hz, 1H), 3.68-3.75 (m, 1H), 3.48-3.64 (m, 3H), 2.14 (d, J=13.1 Hz, 1H), 1.81-1.93 (m, 2H), 1.51-1.70 (m, 3H) ppm; $^{13}$C NMR (100 Mz, DMSO-$d_6$): δ 156.6, 136.4, 128.8, 128.3, 128.0, 106.7, 83.0, 69.7, 54.8, 48.6, 46.7, 29.5, 26.5, 15.0 ppm; HRMS (EI+) calculated value: $C_{16}H_{19}N_3O_3$ (M+), 301.1426; calculated value: 301.1429.

Example 9

Synthesis of 10-(4-chlorobenzyl)-4-nitro-9-oxa-11,12-dihydroimidazo-[2,3-a]-bicyclo-[3,3,1]-non-3-ene (the compound 2d)

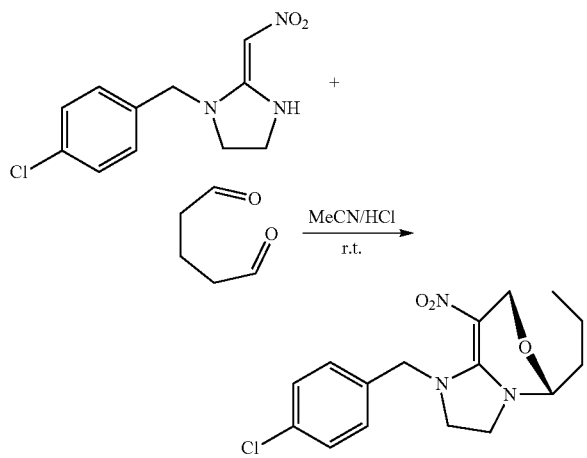

The preparation method is similar to the above method. The solvent was removed under reduced pressure, and column chromatography separation was performed (eluent: dichloromethane/acetone=3/1 (v/v)) to obtain a pale yellow solid in powder. Yield: 70%; mp=156.9-158.3° C.; $^1$H NMR (400 Mz, DMSO-$d_6$): δ 7.29-7.34 (m, 4H), 5.33 (d, J=4.0 Hz, 1H), 5.05 (d, J=15.1 Hz, 1H), 4.96 (s, 1H), 4.75 (d, J=15.1 Hz, 1H), 3.66-3.73 (m, 1H), 3.55-3.60 (m, 3H), 2.14 (d, J=13.6 Hz, 1H), 1.82-1.95 (m, 2H), 1.51-1.71 (m, 3H) ppm; $^{13}$C NMR (100 Mz, DMSO-$d_6$): δ 156.5, 134.9, 133.8, 129.7, 129.0, 106.8, 83.0, 69.6, 54.4, 48.9, 46.6, 29.6, 26.5, 15.0 ppm; HRMS (EI+) calculated value: $C_{16}H_{18}N_3O_3^{35}Cl$ (M+), 335.1037; calculated value 335.1044. Calculated value: $C_{16}H_{18}N_3O_3^{37}Cl$ (M+), 337.1007; calculated value 337.1036.

Example 10

Synthesis of 10-(((tetrahydrofuran-3-yl)methyl)-4-nitro-9-oxa-11,12-dihydroimidazo-[2,3-a]-bicyclo-[3,3,1]-non-3-ene (the compound 2e)

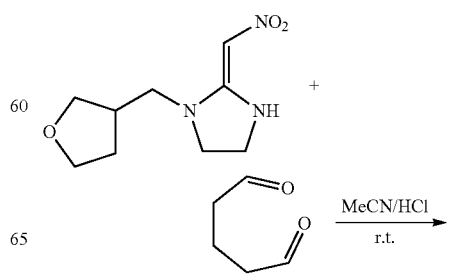

-continued

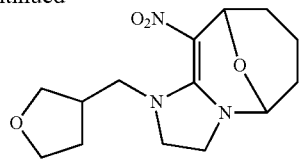

1.065 g of 1-((tetrahydrofuran-3-yl)methyl)-2-(-nitromethylene)-1-imidazoline (0.005 mol), 3 mL of 25% aqueous glutaraldehyde, and a catalytic amount of HCl were placed in a 50-mL round-bottomed flask. The system was stirred at room temperature, and the reaction was monitored by TLC. After the reaction was completed, the solvent was removed, and column chromatography separation was performed to obtain a pure, pale yellow product in powder. The yield was 36%.

mp=115.3-116.9° C.; $^1$H NMR (400 Mz, DMSO-d$_6$): δ 5.11 (s, 1H), 5.00-5.03 (m, 1H), 4.18 (d, J=3.2 Hz, 2H), 4.05-4.25 (m, 2H), 3.85-3.96 (m, 4H), 2.25 (m, 1H), 1.66-1.81 (m, 4H), 1.63-1.64 (m, 2H), 1.57-1.59 (m, 2H), 1.51-1.55 (m, 1H), 1.32-1.44 (m, 1H) ppm; $^{13}$C NMR (100 Mz, DMSO-d$_6$): δ 81.7, 80.6, 78.5, 68.9, 50.0, 49.7, 46.9, 44.6, 36.8, 33.9, 28.8, 27.2, 17.8, 14.8 ppm; HRMS (EI+) calculated value: $C_{14}H_{21}N_3O_4$ (M$^+$), 295.1532; measured value 295.1598.

Example 11

Measuring the Insecticidal Activity of the Compounds of the Present Invention (1) Insecticidal Activity Against Aphids Aphids, which belong to the Homoptera and have piercing-sucking mouth parts, are a common pest for agricultural crops. *Aphis craccivora* was used as the subject, and a dipping method was employed for testing.

Testing method: Each sample was precisely weighed, and 2 mL of DMSO and 18 mL of water were added respectively; then, three drops of the emulsion agent 200I were added to form a testing liquid; a blank was also prepared by adding three drops of emulsion agent 220I to 2 mL of DMSO and 18 mL of water. Broad bean leaves adhered by a certain number of insects were immersed in the testing liquid for three to five seconds, then removed and air-dried; the insects were moved into a clean container together with feed, and the container was placed in a dry, thermostatic recovery room. After 24 hours, the number of dead insects was checked. The results are shown in Table 1.

(2) Insecticidal Activity Against *Nilaparvata lugens*

*Nilaparvata lugens*, which belongs to the Homoptera and has piercing-sucking mouth parts, is a common pest for agricultural crops. *Nilaparvata lugens* was used as the subject, and the micro-drip measurement method reported by Nagata was employed for testing.

Operation procedure: Unmated winged females two to three days after eclosion were selected as the test subjects; the compounds were diluted in acetone to a series of concentrations. The insects were paralyzed by carbon dioxide, and the liquid (0.08 μL) was dripped onto the pronotum of the insects using a manual micro-dripper (Burkard Manufacturing Co., Ltd., Rickmansworth, UK). Each of the concentrations was used to treat about 30 insects in triplicate. Acetone was used as the control. The treated adult insects were cultured on rice seedlings grown without soil in an incubator (20×20×10 cm), where the temperature was controlled at 25±1° C. with 16/8 hours of light and dark cycle. The results were checked after 48 hours, and the LD$_{50}$ was calculated using a standard probability analysis method. The results are shown in Table 2.

(3) Insecticidal Activity Against Armyworms

Second instar *Pseudaletia separata* Walker larvae were used as the subjects and the dipping method was employed for testing.

*Pseudaletia separata* Walker, which is a very important lepidopterans pest of various grains, can be suitably used in various of applications, for example, in the study of toxicity, such as the stomach toxicity, contact poisoning, comprehensive and residual effects of insecticides, and other aspects of insect toxicology, as well as the screen test for new compounds. *Pseudaletia separata* Walker extermination activity was tested in accordance with a method reported in the literature.

Operation procedure of the leaf-dipping method: Each sample was precisely weighed, and 2 mL of DMSO and 18 mL of water were added respectively; and then, three drops of the emulsion agent 2001 (procured from Shanghai Nongyaochang Co., Ltd.) were added to form the test liquid. A blank was also formulated by adding three drops of the 2201 emulsion agent to 2 mL of DMSO and 28 mL of water. Fresh corn leaves were torn into small pieces and immersed for about five seconds in the liquid, then removed, air-dried, and placed in a 100-mL jar. About 20 2nd instar larvae were introduced into the jar. The jar was closed using white gauze and a rubber band, and the larvae were fed with corn soaked with the liquid continuously. The mortality rate of the larvae was checked after five days. The requisite temperature was 22° C. to 27° C., humidity 70% to 80%. There was no need to correct the mortality rates for each treatment if the blank mortality rate was 5% or less; however, if the control mortality rate was 5% to 20%, Abbott's correction should be used for the mortality rates for each treatment. Abbott's formula:

Corrected mortality rate=[(treated mortality rate−control mortality rate)/(100−control mortality rate)× 100].

TABLE 1

Insecticidal activities of target compounds against aphids and *Pseudaletia separata* Walker

| Compound | *Aphis craccivora* | | *Pseudaletia separata* Walker | |
| --- | --- | --- | --- | --- |
| | Mortality rate (%, 500 mg L$^{-1}$) | LC$_{50}$ (mmol L$^{-1}$) | Mortality rate (%, 500 mg L$^{-1}$) | LC$_{50}$ (mmol L$^{-1}$) |
| 4 | 78.1 | n.t. | 100 | 106.97 |
| 5 | 97.7 | n.t. | 100 | n.t. |
| 6 | 100 | 5.19 | 100 | 15.26 |
| 1a | 100 | 1.52 | 100 | 12.5 |
| 1b | 100 | n.t. | 100 | n.t. |
| 1c | 13.6 | n.t. | 0 | n.t. |
| 1d | 95.7 | n.t. | 0 | n.t. |
| 2a | 87.3 | n.t. | 0 | n.t. |
| 2b | 98.2 | n.t. | 0 | n.t. |
| 2c | 55.6 | n.t. | 0 | n.t. |
| 2d | 38.9 | n.t. | 0 | n.t. |
| Imidacloprid | 100 | 8.93 | 100 | 38.7 |

TABLE 2

Activities of compounds against susceptible and resistant *Niloparvata lugens*

| Strain | Compound | Toxicity curve | $LD_{50}$ (ng/pest) | Relative toxicity | Magnitude of resistance |
|---|---|---|---|---|---|
| Susceptible strain | 1a | y = 7.3127 + 2.0474x | 0.0742 ± 0.0106 | 1.77 | 1.00 |
| | 2a | y = 3.9543 + 1.6936x | 4.1440 ± 0.6136 | 0.32 | 1.00 |
| | Imidacloprid | y = 7.1823 + 2.4778x | 0.1316 ± 0.0154 | 1.00 | 1.00 |
| Resistant strain | 1a | y = 5.4068 + 1.3225x | 0.4925 ± 0.0811 | 50.00 | 6.64 |
| | 2a | y = 3.1320 + 1.4613x | 18.9795 ± 2.3501 | 1.17 | 4.58 |
| | Imidacloprid | y = 2.5873 + 1.7930x | 22.1614 ± 3.7522 | 1.00 | 168.40 |

The activities of the target compounds on aphids, *Pseudaletia separata* Walker, and *Niloparvata lugens* were tested, and the results are shown in Tables 1 and 2. It can be seen from Tables 1 and 2 that the oxabridged heterocyclic compound 1a possesses very high activity which is much higher than that of imidacloprid: $LC_{50}$ against aphids is 1.52 mg $L^{-1}$, and $LC_{50}$ against *Pseudaletia separata* Walker is 12.5 mg $L^{-1}$. Even more importantly, the activity of the compound 1a against susceptible *Niloparvata lugens* is generally the same as that of imidacloprid, and the activity thereof against imidacloprid-resistant *Niloparvata lugens* is 50 times that of imidacloprid. Compound 1a has relatively weak activity. Interestingly, the activities of the oxabridged heterocyclic compounds 2a to 2c, which are constructed from glutaraldehyde, were much weaker, and some compounds were effective only against aphids. An analysis of the crystalline structures of the compounds 1a and 2a shows that the compounds 1a and 2a have different oxabridged configurations, where oxabridges are opposite in orientation; this difference can be very clearly observed by superimposing the two molecules. This difference in the oxabridged structures may be responsible for the markedly different activities of the compounds 1a and 2a.

Example 12

Research of the Mechanism of Action of the Compound (1a)

The compound (1a) was separately subjected to electrophysiological testing and isotope marker substitution testing. Compound (1a) can inhibit agonist response, compound (1a) has no agonistic action on the nicotinic acetylcholine receptors of *Periplaneta americana* nor on the N1 α 1/β 2 receptors expressed by the oocytes, and compound (1a) can inhibit the agonist response to acetylcholine. These experiments demonstrate that the compound is an antagonist of the nicotinic acetylcholine receptor (nAChRs).

Example 13

Preparing Insecticide Compositions Containing the Compounds of the Present Invention (a) Oily Suspension The following components were prepared: 25 wt % of any one of compounds 1a to 1e and 2a to 2e; 5 wt % of polyoxyethylene sorbitol hexaoleate; and 70 wt % of a higher aliphatic hydrocarbon oil. All of the components were milled together in a sand mill until the particle size of solid granules were reduced to less than about five microns. The resultant viscous suspension can be used directly, or can be used upon being emulsified in water.

(b) Aqueous Suspension

The following components were prepared: 25 wt % of any one of compounds 1a to 1e and 2a to 2e; 3 wt % of hydrate attapulgit; 10 wt % of calcium lignosulfate; 0.5 wt % of sodium dihydrogen phosphate, and 61.5 wt % of water. All of the components were milled together in a ball mill until the particle size of solid granules were reduced to less than about ten microns. The aqueous suspension can be used directly.

(c) Bait

The following components were prepared: 0.1-10 wt % of any one of compounds 1a to 1e and 2a to 2e; 80 wt % of wheat flour; and 19.9-10 wt % molasses. These components were thoroughly mixed, and shaped as needed. The edible bait can be distributed to a place infested by sanitary pests, for example a domestic or industrial place, such as a kitchen, hospital, store, or outdoor area, thereby controlling pest through oral ingestion.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

SEQUENCE LISTING (Not applicable)

The invention claimed is:

1. A compound of Formula (A), or an optical isomer or agrochemically acceptable salt thereof:

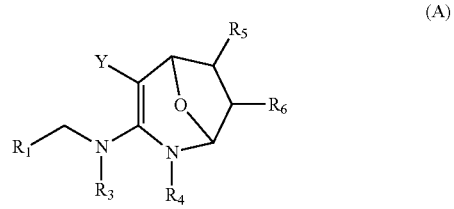

wherein:

R₁ is a nitrogen-, an oxygen-, and/or a sulfur-containing five- or six-membered heterocycle; a halogenated nitrogen-, oxygen-, and/or sulfur-containing five- or six-membered heterocycle; or a substituted or unsubstituted phenyl, wherein the substituents are selected from one or more of the following groups: a halogen, a $C_{1-4}$ halogenated alkyl, or a $C_{1-4}$ chlorinated alkoxy;

R₃ and R₄ together form —CH₂—CH₂—,

R₅ and R₆ are hydrogen, saturated or unsaturated $C_{1-4}$ alkyl, halogen, saturated or unsaturated $C_{1-8}$ alkoxy, saturated or unsaturated $C_{1-4}$ halogenated alkoxy, C(O)$C_{1-4}$ alkyl, C(O)O$C_{1-8}$ alkyl, S(O)₂O$C_{1-4}$ alkyl, phenyl, or benzyl; and Y is nitro, cyano, trifluoromethyl, trifluoroacetyl or trifluoromethanesulfonyl.

2. The compound or an optical isomer or agrochemically acceptable salt thereof according to claim 1, wherein the compound is selected from the following group:

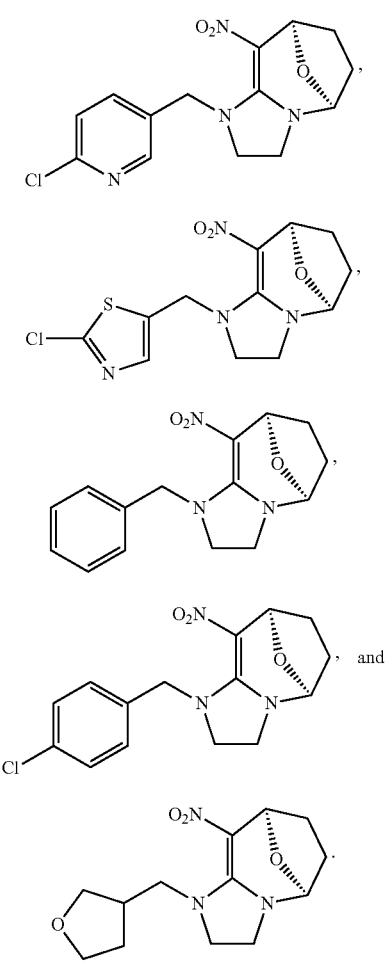

3. The compound, or an optical isomer or agrochemically acceptable salt thereof according to claim 1, wherein the compound is selected from the following group:

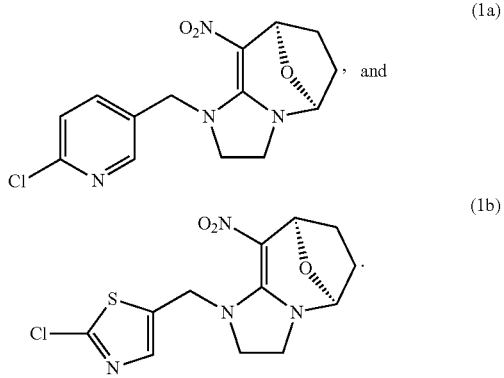 [SMILES: O=[N+]([O-])C1=C2N(Cc3ccc(Cl)nc3)CCN2[C@@H]2CC[C@H]1O2 ; "," ; "and" ; O=[N+]([O-])C1=C2N(Cc3cnc(Cl)s3)CCN2[C@@H]2CC[C@H]1O2 ; "."]

4. The compound according to claim 1, wherein the compound is selected from the group consisting of the following compounds:
- 9-((6-chloropyrid-3-yl)methyl)-4-nitro-8-oxa-10,11-dihydroimidazo-[2,3-a]-bicyclo-[3.2.1]-oct-3-ene;
- 9-((2-chlorothiazol-5-yl)methyl)-4-nitro-8-oxa-10,11-dihydroimidazo-[2,3-a]-bicyclo-[3.2.1]-oct-3-ene;
- 9-benzyl-4-nitro-8-oxa-10,11-dihydroimidazo-[2,3-a]-bicyclo-[3.2.1]-oct-3-ene;
- 9-(4-chloro-benzyl)-4-nitro-8-oxa-10,11-dihydroimidazo-[2,3-a]-bicyclo-[3.2.1]-oct-3-ene; and
- 9-((tetrahydrofuran-3-yl)methyl)-4-nitro-8-oxa-10,11-dihydroimidazo-[2,3-a]-bicyclo-[3.2.1]-oct-3-ene.

5. An agrochemical composition, comprising:
(a) 0.001 to 99.99 wt % of the compound according to claim 1, an optical isomer or agrochemically acceptable salt thereof, or a combination thereof; and
(b) an agrochemically acceptable carrier and/or excipient.

6. The agrochemical composition according to claim 5, wherein, the agrochemically acceptable carrier is a solid.

7. The agrochemical composition according to claim 5, wherein, the agrochemical composition is formulated as a solution, emulsion, suspension, powder, foam, paste, granule, aerosol, micro-capsule in polymer, coating complex for seed, preparation used with a combustion device, or an ultra low volume cold mist or warm mist preparation.

8. The agrochemical composition according to claim 5, wherein the compound is selected from the group consisting of:
- 9-((6-chloropyrid-3-yl)methyl)-4-nitro-8-oxa-10,11-dihydroimidazo-[2,3-a]-bicyclo-[3.2.1]-oct-3-ene;
- 9-(2-chlorothiazol-5-yl)methyl)-4-nitro-8-oxa-10,11-dihydroimidazo-[2,3-a]-bicyclo-[3.2.1]-oct-3-ene;
- 9-benzyl-4-nitro-8-oxa-10,11-dihydroimidazo-[2,3-a]-bicyclo-[3.2.1]-oct-3-ene;
- 9-(4-chloro-benzyl)-4-nitro-8-oxa-10,11-dihydroimidazo-[2,3-a]-bicyclo-[3.2.1]-oct-3-ene; and
- 9-((tetrahydrofuran-3-yl)methyl)-4-nitro-8-oxa-10,11-dihydroimidazo-[2,3-a]-bicyclo-[3.2.1]-oct-3-ene.

9. A method of pest control comprising applying the agrochemical composition according to claim 5 to agricultural pests, sanitary pests or pests endangering the health of animals.

10. The method according to claim 9, wherein the pests are agricultural pests, and the method comprises applying the agrochemical composition to plants suffering from pests or susceptible to suffering from pests, the surrounding soil or environment thereof.

11. The method according to claim 9, wherein the agrochemical composition is applied to one or more seeds.

12. The method according to claim 11, wherein the agrochemical composition is applied to the seeds as a coating of the seeds.

13. A method for exterminating or preventing agricultural pests, sanitary pests, and pests endangering the health of animals comprising applying the agrochemical composition according to claim 5 to agricultural pests, sanitary pests, and pests endangering the health of animals.

14. A method for preparing the compound of Formula (A) according to claim 1, the method comprising:

reacting a compound of Formula (a):

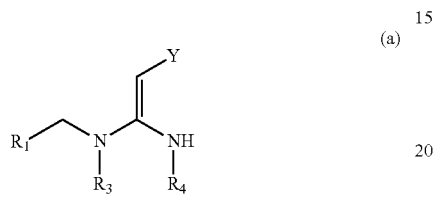
(a)

with a compound of Formula (b):

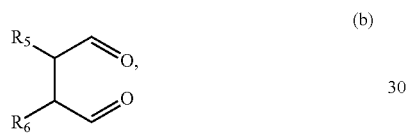
(b)

at room temperature in the presence of an acid catalyst.

15. The method according to claim 14,
wherein when the compound of Formula (a) is

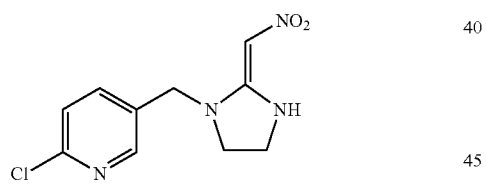

and the compound of Formula (b) is

the method comprises reacting

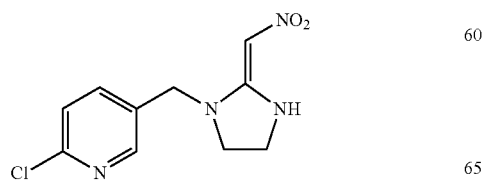

with

for 2 to 24 hours in acetonitrile at room temperature in the presence of an acid catalyst, so as to obtain a compound of Formula (1a):

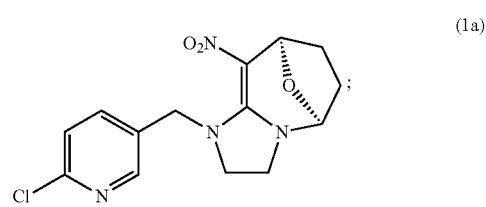 [SMILES: O=[N+]([O-])C1=C2N(Cc3ccc(Cl)nc3)CCN2[C@@H]2CC[C@H]1O2]
(1a)

wherein when the compound of Formula (a) is

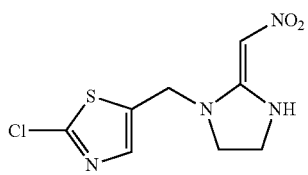 [SMILES: O=[N+]([O-])/C=C1\NCCN1Cc1cnc(Cl)s1]

and the compound of Formula (b) is

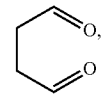

the method comprises reacting

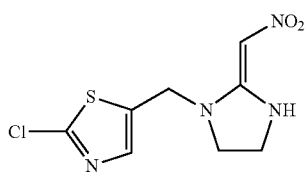 [SMILES: O=[N+]([O-])/C=C1\NCCN1Cc1cnc(Cl)s1]

with

10 for 2 to 24 hours in acetonitrile at room temperature in the presence of an acid catalyst, so as to obtain a compound of the Formula (1b):

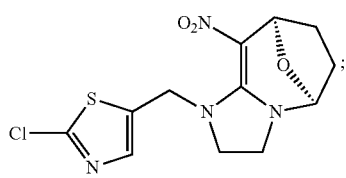

wherein when the compound of Formula (a) is

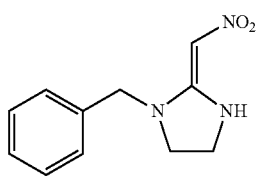 [SMILES: O=[N+]([O-])/C=C1\NCCN1Cc1ccccc1]

and the compound of Formula (b) is

the method comprises reacting

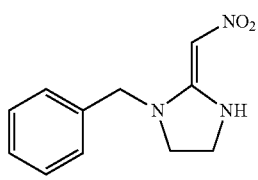 [SMILES: O=[N+]([O-])/C=C1\NCCN1Cc1ccccc1]

with

for 2 to 24 hours in acetonitrile at room temperature in the presence of an acid catalyst, so as to obtain a compound of the Formula (1 c):

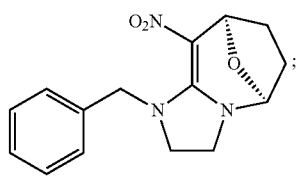

wherein when the compound of Formula (a) is

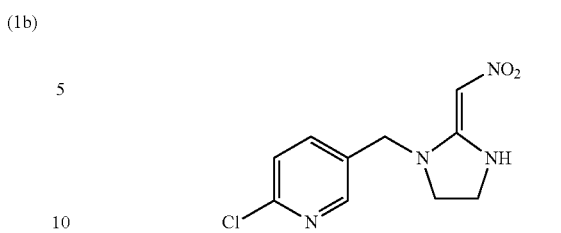

and the compound of Formula (b) is

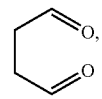

the method comprises reacting

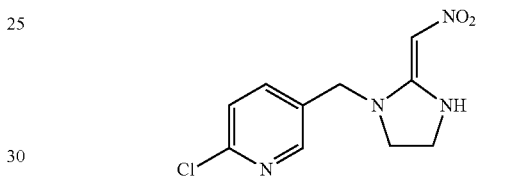

with

for 2 to 24 hours in acetonitrile at room temperature in the presence of an acid catalyst so as to obtain a compound of the Formula (1d):

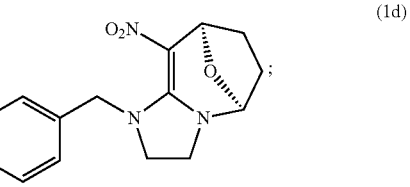

and wherein when the compound of Formula (a) is

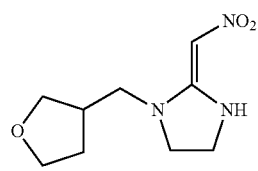 [SMILES: O=[N+]([O-])/C=C1\NCCN1CC1CCOC1]

and the compound of Formula (b) is
the method comprises reacting
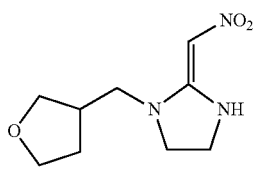
with
for 2 to 24 hours in acetonitrile at room temperature in the presence of an acid catalyst so as to obtain a compound of the Formula (1e),
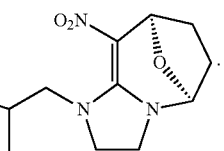
(1e)
* * * * *